(12) United States Patent
Garth et al.

(10) Patent No.: US 6,315,746 B1
(45) Date of Patent: *Nov. 13, 2001

(54) CERVICAL SPINAL ORTHOSIS HAVING A MOVABLE CHEST PLATE

(75) Inventors: Geoffrey Campbell Garth, Long Beach; John Curtis Hamilton, Rancho Santa Margarita, both of CA (US)

(73) Assignee: International Healthcare Devices, Long Beach, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/031,731

(22) Filed: Feb. 27, 1998

(51) Int. Cl.$^7$ ............................................. A61F 5/00
(52) U.S. Cl. ................................. 602/18; 128/DIG. 23
(58) Field of Search ............... 602/17–19; 128/DIG. 23, 128/DIG. 19; 2/455, 459–463, 468, 44–45; 482/10

(56) References Cited

U.S. PATENT DOCUMENTS

| | | | |
|---|---|---|---|
| 2,223,276 | * 11/1940 | Ward | 602/18 |
| 2,692,595 | * 10/1954 | Blair . | |
| 2,820,455 | * 1/1958 | Hall | 602/18 |
| 2,904,040 | * 9/1959 | Hale | 602/18 |
| 3,548,817 | * 12/1970 | Mittasch . | |
| 3,776,224 | * 12/1973 | McFarland | 602/18 |
| 3,855,631 | * 12/1974 | Ettinger | 2/468 |
| 4,502,471 | * 3/1985 | Owens | 602/18 |
| 4,590,622 | * 5/1986 | Wolfe et al. | 2/462 |
| 4,628,913 | * 12/1986 | Lerman | 602/18 |
| 4,677,969 | * 7/1987 | Calabrese | 602/18 |
| 4,899,736 | * 2/1990 | Nesbitt . | |
| 5,433,696 | * 7/1995 | Osti | 602/18 |
| 5,964,722 | * 10/1999 | Goralnik | 602/18 |

* cited by examiner

Primary Examiner—Denise Pothier
(74) Attorney, Agent, or Firm—Kenyon & Kenyon

(57) ABSTRACT

A cervical spine orthosis includes a neck collar, a load bearing chest plate and a support strut coupling the neck collar to the load bearing chest plate. The support strut can be pivotally connected to the neck collar so that when necessary the entire chest plate and support strut can be moved relative to the neck collar so as to permit access to a chest area of the patient without completely removing support for the patient's head and neck.

11 Claims, 3 Drawing Sheets

CERVICAL SPINAL ORTHOSIS HAVING A MOVABLE CHEST PLATE

BACKGROUND OF THE INVENTION

The present invention is directed to a cervical spine orthosis device. More particularly, the present invention is directed to a device which provides a neck collar, providing support to a patient's head, connected to a load bearing chest plate where the chest plate can be moved without completely removing support for the patient's head.

There are a number of prior art neck collars that provide support for a patient's head where it is desirable to restrict the motion of the head and neck. The known neck collars provide varying degrees of restriction with respect to flexion, extension or side-to-side (rotational) movement. Such motion restriction can be critical where damage to the cervical spine is of concern. Such neck collars are commonly used where the wearer has been exposed to some trauma which could result in a cervical spine injury that might be exacerbated by movement of the patient's head or after surgery to the spine. Examples of such collars include the collars disclosed in U.S. Pat. No. Re 32,219 and U.S. Pat. No. 5,097,824. The entire disclosures of these two patents are hereby incorporated by reference. The latter patent describes a collar that is particularly adaptable to extended-wear use. The design provides significant motion restriction while providing comfort to a user that must wear the collar for an extended period of time.

The prior art also contains alternative structures that provide some sort of motion restriction. In particular, a number of devices are available that provide a bracing structure that can be worn by the patient. The brace includes a harness portion that is supported on the patient's torso, a chin support and a rigid bar attached to the chin support and the harness. In these designs, as exemplified in U.S. Pat. No. 3,724,452, the motion restriction is solely dependent on the fixed relationship between the chin support and the harness as provided by the rigid bar.

It is also known to provide support for a patient's neck by attaching a neck collar to a bracing structure which is in contact with the torso of the patient. Examples of such collar/brace combinations are shown in U.S. Pat. Nos. 4,677,969 and 4,515,153. Looking at the '969 patent a collar, for example 10 in FIG. 1 , is connected via a connecting member, for example 54 , to a front plate, such as 56 . The collar is connected to the supporting member by rivets, e.g., 62 . The collar/brace combination in the '153 patent is very similar. The patents indicate that the connecting rivets can only be removed using a tool such as a pair of pliers and are designed so that they cannot be removed by the patient. One limitation of the arrangement disclosed in these patents is that the supporting member 54 and the front plate 46 are difficult to remove. In certain circumstances, such as when the need arises to perform cardio-pulmonary resuscitation (CPR) on a patient wearing such an apparatus, it is difficult to access the chest region in view of the presence of the supporting member and the attachment of the supporting member to the collar using rivets that are difficult to remove. Another limitation on this arrangement is the configuration of the collar itself and the extent to which it would provide sufficient support for the head and neck in the absence of the brace if the brace could be removed.

It is desirable to provide a supporting mechanism which provides a collar and an additional support including a load bearing chest plate where the chest plate is easily movable relative to the collar so as to provide access to the chest area. The chest area should be made accessible without removing all of the support that provides head and neck motion restriction.

SUMMARY OF THE INVENTION

The present invention provides a cervical spine orthosis device which includes a neck collar that supports a patient's head and neck and an additional supporting mechanism attached to the collar. In one embodiment the additional supporting member includes a supporting strut that is pivotally connected to the collar and is also attached to a load bearing chest plate. In one embodiment the chest plate can be connected to a backplate via strapping mechanisms. The load bearing chest plate provides additional support via the supporting strut. This further restricts flexion and rotation motion when worn by a patient. Because the supporting strut is pivotally connected to the collar, however, the chest plate can be decoupled from the backplate and can be quickly rotated away from the patient's chest to provide access to the chest area should such access be needed for any reason, including for example, performing CPR. The neck collar still provides head and neck motion restriction despite lack of support from the chest plate.

One example of the supporting strut mechanism is constituted by a single rod that is detachably and/or adjustably connected to the load bearing chest plate while having pivotal attachments to a front portion of the neck collar in an area adjacent to a portion of that collar which makes contact with an upper chest area of the patient.

In a further refinement of the invention the neck collar includes a front portion having at least two pieces where a first piece is a chin/jaw support and a second piece supports the chin/jaw support and is in contact with an upper chest area of a patient. The support strut can be attached to the second piece, thereby providing additional support to the head and neck via the two piece arrangement.

In a further embodiment of the present invention, the collar includes a back portion having an occipital support. A second support strut can be provided connecting the back portion of the collar to the backplate. Thus, the backplate also acts as a load bearing member. As such it provides additional support for the back of the patient's head and thereby further limits extension. The second support strut can also be connected in a pivotal fashion to the back portion of the collar thereby permitting detachment of the backplate from the chest plate and subsequent movement of the backplate relative to the back portion of the neck collar.

Further advantages and details of the present invention will be understood from the detailed description that follows.

DETAILED DESCRIPTION

Figure 1:
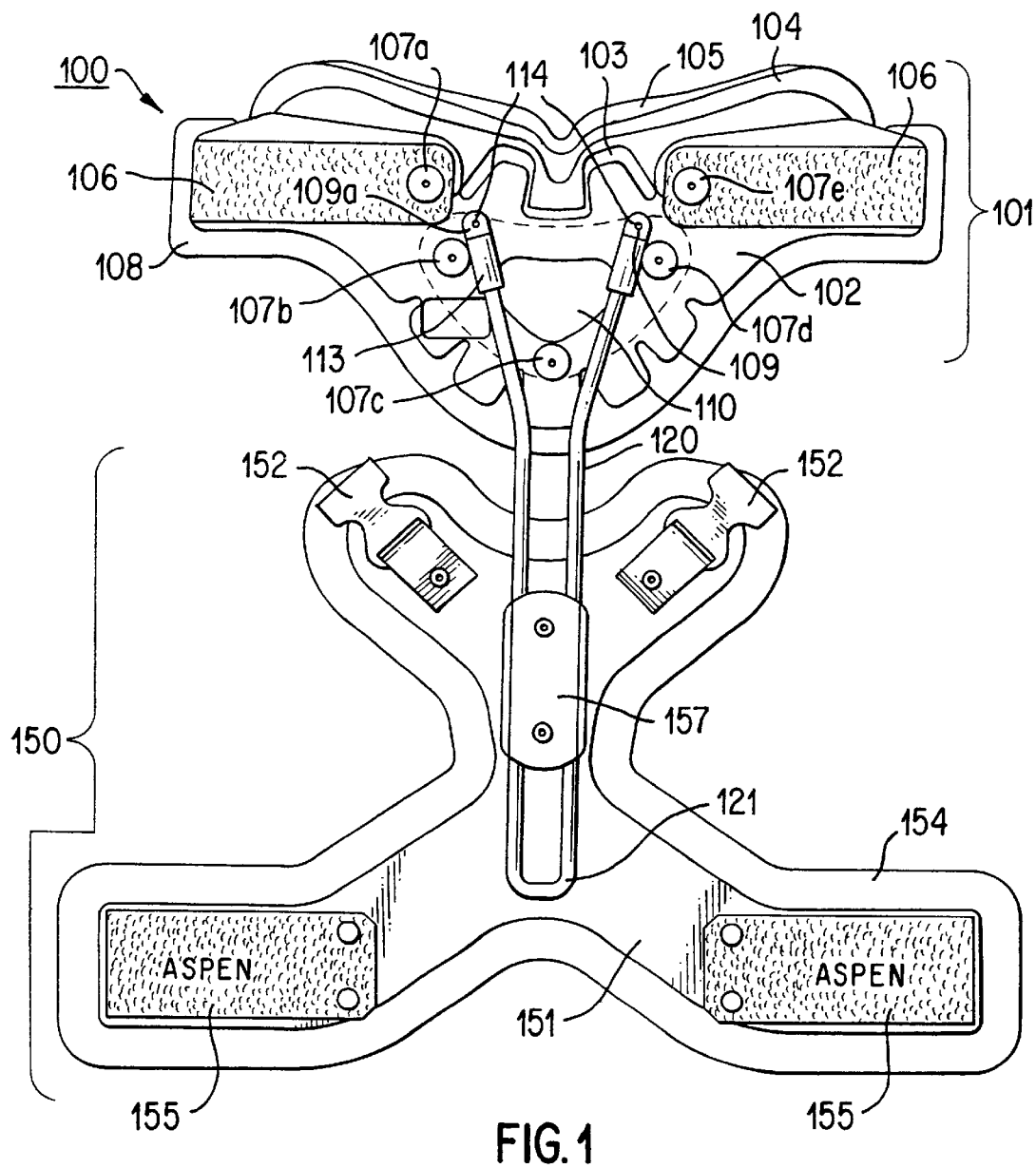
FIG. 1 illustrates a front view of a front section of a cervical spine orthosis device in accordance with an embodiment of the present invention.

The present invention will now be described with reference to the drawing figures in which those items bearing the same reference numerals are the same throughout the drawings.

The present invention provides a neck collar for restricting the motion of a patient's head and neck to prevent at least flexion and rotation. The collar can also be provided to prevent extension. An additional supporting mechanism is provided in connection with the collar so as to further limit the motion of the patient's head and neck. In particular, the collar is connected to a support strut mechanism that is coupled to a load bearing chest plate. Together the support strut and the load bearing chest plate provide additional support to the collar and hence to the patient's head and neck.

An example of a front portion of a cervical spine orthosis in connection with the present invention is illustrated in FIG. 1 as 100. The front portion of the orthosis includes a front portion of a collar 101 a support strut 120 and a load bearing chest plate 150.

The front portion of the collar, 101, can be constituted by a collar such as that described and disclosed in U.S. Pat. No. Re 32,219 and U.S. Pat. No. 5,097,824 which have been incorporated by reference. The elements shown for the collar in FIG. 1 include a first support portion 102 which is constituted by a stiff plastic material such as polyethylene. A second piece of stiff plastic material can be attached immediately behind the first front portion as element 103 in a front central portion of the neck collar. This element provides additional stiffening to the collar in a region where a hole that permits tracheotomies, 110, is provided. A chin/jaw support portion 104 is connected to the first support portion 102 by two fasteners 107a and 107e which also fasten a first part of a VELCRO fastener 106 to either side of the front portion of the collar. Additional fasteners similar to that of 107a and 107e may be provided to further connect the chin/jaw support 104 to the front portion 102, however, no such additional fasteners are illustrated in FIG. 1. The fasteners 107a and 107e can be fixed rivets or they can be detachable fasteners such as, but not limited to, Christmas tree fasteners. The fasteners simply need to provide a strong attachment for the chin support/front portion combination. Any combination of such fasteners might be utilized in connection with fastening the chin/jaw support to the first support portion 102. Similarly, fasteners 107b, 107c and 107d are used to fasten the additional support, the second piece of stiff plastic material 103, to the first support portion 102. These fasteners 107b, 107c and 107d can be the same as or different from fasteners 107a and 107e. A cushioning pad 105 can be attached to the chin/jaw support 104. This attachment could be a fixed attachment such as for example by gluing the pad to the support or detachable. A detachable connection could be provided, for example, by VELCRO fasteners that would allow the easy removal and replacement of these pads. The pads can be constituted by materials such as an ester foam. When worn the front portion of the collar is arranged such that the first support portion provides support to the chin/jaw support portion and rests either directly or indirectly (with an intervening soft pad) on the upper torso of the patient. This arrangement restricts flexion and rotational movement.

A support strut mechanism is coupled to the first support portion 102 of the neck collar 101. In the present embodiments the coupling is provided by two pivotal or hinged typed attachments 109 and 109a. The attachments 109 and 109a may be constituted by a rivet, not shown, that passes through a hole in support portion 102 and a corresponding hole, in the end of the support 120 and/or alternatively, as in the illustrated example, a hole 114 in a cap 113 attached to the end of support 120. The cap can be made of plastic. The pivotal attachments permit the strut mechanism to be rotatable in relation to the neck collar 101. In the example shown the strut mechanism is constituted by a single rod which is bent to form a U-shape at a region 121 adjacent to chest plate 150. Furthermore, the two points of contact with the collars are on either side of center and are in a region of the first support portion of the front of the collar near its contact with the patient's upper torso. This attachment placement is advantageous in that is more efficiently spreads out the forces applied by the strut. Those forces are spread out over the front portion of the collar which provides a broader based of support than if the strut was coupled to the chin/jaw support in a single place such as directly below the chin as is done in other brace configurations. By spreading out the forces this arrangement slows the breakdown of the skin along the chin/jaw support by avoiding undo pressure on that skin area. Alternative configurations for the support mechanism include: a single bar with pivotal attachment point(s) to the front portion of the collar; or multiple bars might be provided coupling the front portion of the collar 102 to the load bearing chest plate 150. A hinge-type mechanism might be usable for the attachment as well. Other strut mechanisms can also provide the desired additional support for the collar. Furthermore, although not shown in the drawings the strut mechanism could be attached to the chin/jaw support rather than the first support portion of the front of the collar. The strut again could be arranged to better take into account the applied forces in an attempt to reduce skin breakdown. In the illustrated embodiment the pivotal attachment points facilitate a movement of the strut and chest plate with respect to the collar. Other arrangements that also permit such relative movement, without specifically requiring a pivotal attachment are considered to be within the scope of this invention.

In this embodiment of the present invention, the load bearing chest plate 150 includes a chest plate of stiff flexible plastic material such as polyethylene, 151. Snap fasteners 152 are also attached to a top region of the chest plate. The snap fasteners are to be used in conjunction with fastener inserts to position supporting straps over the shoulder of the patient as will be described in connection with FIGS. 2 and 3. Furthermore, an attachment mechanism 157 fastens the support strut 120 to the chest plate. The attachment is adjustable in that the position of the strut mechanism can be adjusted in relation to the chest plate to adjust for the length of the neck and torso of the patient to provide a more appropriate fit. The front portion of the chest plate also can include regions 155 which are to be utilized in connection with a fastening of a chest plate to belt(s) or strap(s) which either surround(s) the torso of the patient or are attached to a backplate such as that shown in FIG. 2. To provide additional comfort to the user, a soft pad 154, made possibly out of the same material as pad 105 can be provided, attached to the stiff flexible plastic material 151, so that the areas in contact with the chest or upper torso region of the patient are contacted by the soft pad portions.

Figure 2:
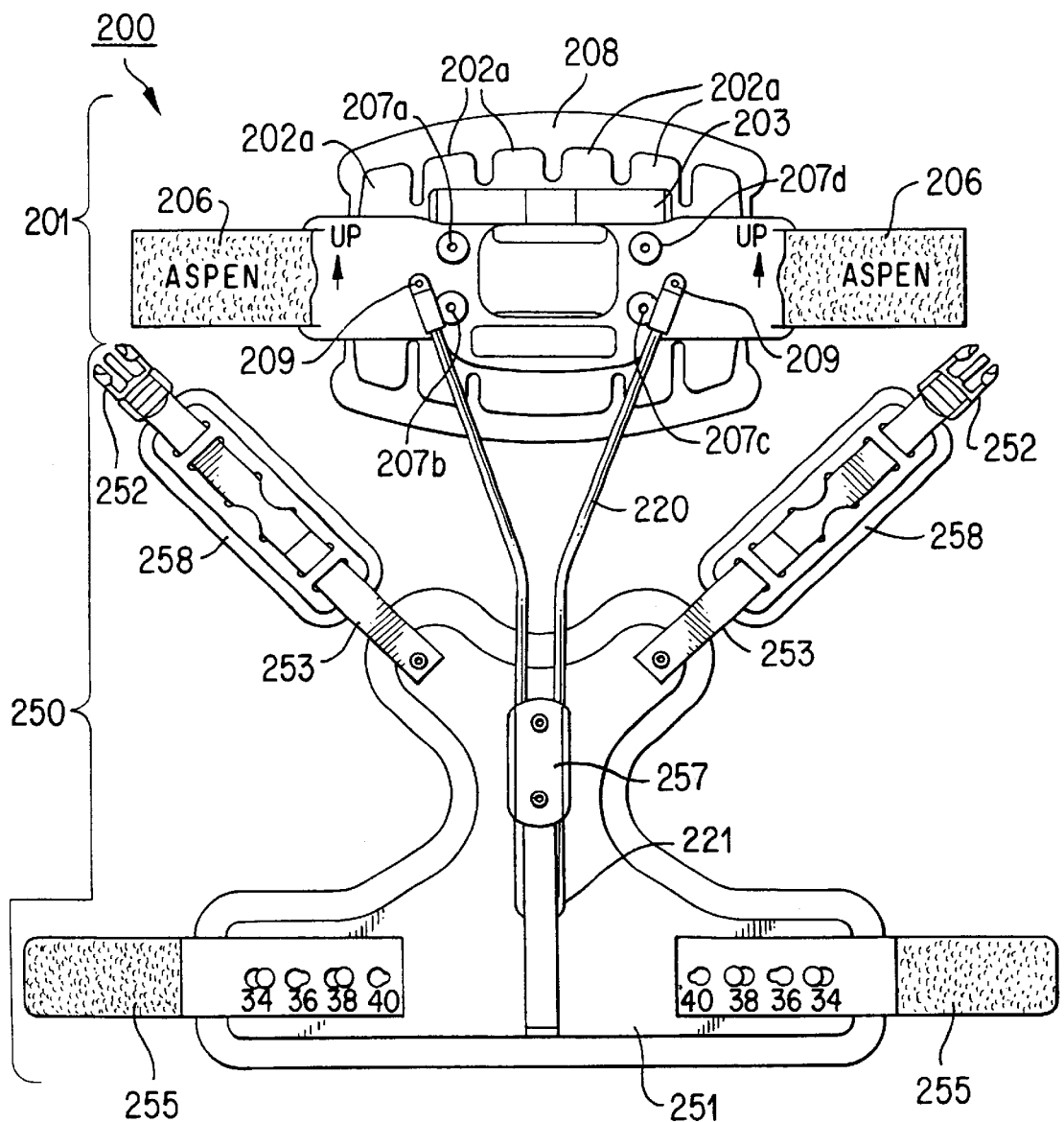
FIG. 2 illustrates a view of a back portion of a cervical spine orthosis in accordance with an embodiment of the present invention.

An example of a back portion of a cervical orthosis device in connection with an embodiment of the present invention is illustrated in FIG. 2. The back portion includes a back portion of a collar, a backplate, and a back support strut mechanism 220. In the illustrated design the collar is a multi-piece collar. The invention could be implemented with a one piece collar but a multi-piece collar design is preferred. Again, the back portion 201 of the collar can be constituted by a back portion of a collar such as that described in either U.S. Pat. No. Re 32,219 or U.S. Pat. No. 5,097,824. In connection with the illustrated embodiment the back portion includes a back support element 202 that includes occipital support fingers, e.g., 202*a*. The back support portion is connected to a back band portion that can be constituted by a stiff flexible plastic material 203 via fasteners 207*a*, 207 *b*, 207*c* and 207*d*. These four fasteners can be of any one of the types described above in connection with the fasteners 107 used on the front portion of the collar. This back band portion 203 is also connected to VELCRO attachment elements 206 that interact with elements 106 on the front portion of the collar so as to provide a fastening of the collar around the patient's neck. A back support strut mechanism 220 is pivotally connected at points 209 to the back band portion 203 of the back portion 201 of the collar. A soft foam pad such as 208 can also be attached to the back support structure 202 so as to provide additional comfort in the course of supporting the back of the patient's head. The back portion of the collar prevents extension motion on the part of the wearer. As described with respect to the pads on the front portion of the orthosis, the pad on the collar may be detachable from the back support element 202 so as to allow the interchangeability or replacement of these soft foam pads. The pad may be constructed of a material such as an ester foam.

The back support strut mechanism 220 is coupled to a back plate 250 by adjustable attachment mechanism 257. The adjustable attachment mechanism allows for the back support strut mechanism to be moved up and down in relation to the backplate to thereby appropriately size the device in relation to the intended user of the device. In the illustrated example the back support strut mechanism is a single rod bent to form a U-shape 221. The back support strut mechanism is not limited to such a construction nor is it limited to being of the same construction as the support strut mechanism of the front portion.

The backplate also has connected thereto elements 255 which are additional portions of VELCRO fasteners which are to fasten to the portions 155 on the chest plate so as to provide a connection between the front and back plate. In an alternative embodiment where the chest plate is used without a backplate, a strap of a material similar to 255 could be used to encircle the patient's torso and attach on either side of the front of the chest plate 155.

Straps 253 are attached to the backplate and are designed to extend over the shoulders of the wearer of the device. The straps have attached thereto fastening elements 252 which interact with fastening elements 152 of the chest plate thereby connecting the straps to the chest plate to provide support for the chest and back plate using the shoulders of the intended user. Although one type of snap fastener, a side clasp buckle is shown, alternative fasteners suitable for connecting straps can also be used and still remain within the scope of this invention. Additionally, the straps can have pad portions 258 attached thereto so as to provide a more comfortable fit over the shoulders of the patient. As with the front chest plate, if the back chest plate is decoupled from the front chest plate then the entire backplate and back support strut mechanism can be moved in relation to the back portion of the collar 201 without completely removing the occipital support for the patient, i.e., the back portion of the collar, even in the absence of assistance from the load bearing back plate, provides occipital support and prevents extension.

Figure 3:
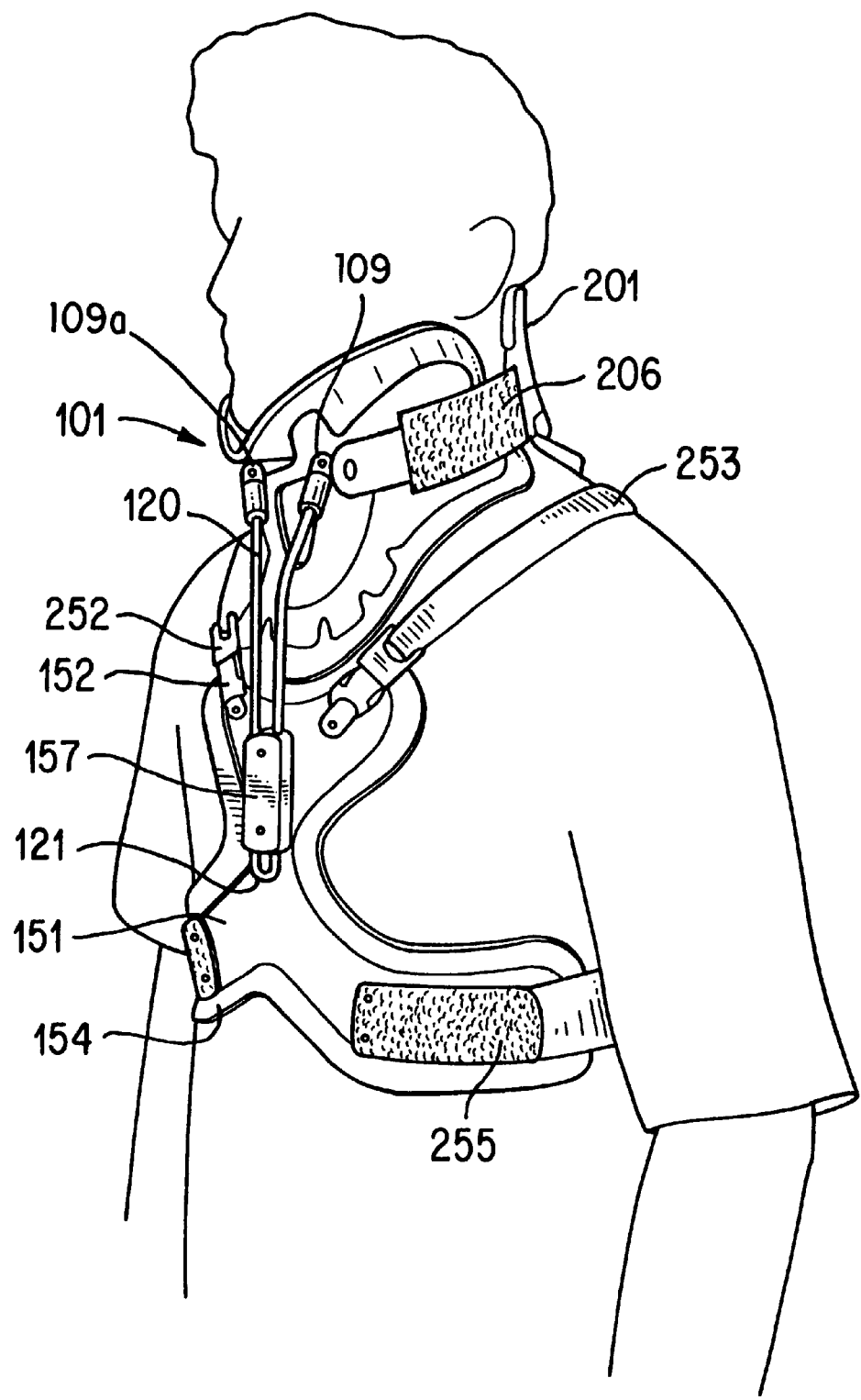
FIG. 3 illustrates a three quarter view of a patient wearing a device assembled from the front and back portions illustrated in FIGS. 1 and 2.

FIG. 3 provides a three quarter perspective drawing of the cervical orthosis described in connection with FIGS. 1 and 2 above. The back and front portions are connected to one another via straps 253, fasteners 252 and 152, strap 255 and fastener region 155 on the chest plate. It can be seen in this figure that the collar provides contact to an upper chest and upper back region of the wearer. More specifically, the first support portion and the back support element of the collar provide support for the chin/jaw support portion of the collar and for the occipital support portion of the back of the collar respectively. Thus, there are two main sources of support that prevent, for example, flexion and rotation movement of the head and neck, namely, first, the collar itself with the front support portion and the chin/jaw support and second, the support strut mechanism in connection with the chest plate which acts as a load bearing element thereby further restricting the motion of the patient's neck and head.

In the event that a patient wearing the cervical orthosis device should need care in either the chest area or the back area, it is possible to detach the chest and back plate elements from each other. Then, presuming chest access is desired the front support strut 120 can be moved along with the chest plate in relation to the neck collar as shown in FIG. 3 so as to provide access to the chest region while the neck collar continues to maintain restrictions on movement of the head and neck. Access can similarly be provided to the back region of the patient if necessary by movement of the back support strut with respect to the back of the collar.

Another advance over the prior art is the relationship between the neck collar and strut mechanism in that the collar can have two front pieces, a chin/jaw support and a supporting member that supports the chin/jaw support. The strut mechanism in one embodiment is connected to the supporting member. This arrangement provides advantages even where the strut is not attached in a pivotal manner. It provides additional degree of support structure, the strut mechanism/chest plate, that could be in effect removed while maintaining head and neck restriction. Also the coupling of the strut mechanism to the collar coupling of the strut mechanism to the collar is arranged to better spread out the forces applied by the strut mechanism to reduce the occurrence of skin damage.

The present invention provides an advance over known support structures in that it maintains restrictions on the motion of a patient's head while enabling movement of a load bearing chest support or back support so as to provide access to a patient's torso without removing all restrictions on head and neck movement.

What is claimed is:

1. A cervical spine orthosis apparatus comprising:
   a neck collar including:
      a first supporting member oriented to contact an upper frontal chest area of a patient when being worn; and
      a chin support rigidly coupled to said first supporting member;
   a pressure bearing chest pad; and
   a support strut pivotally attached to said neck collar and mounted on said pressure bearing chest pad, wherein the support strut is pivotally attached to said first supporting member.

2. The orthosis of claim 1 further comprising:
   a pressure bearing back pad; and
   a second support strut attached to said neck collar and mounted on said pressure bearing back pad.

3. The orthosis of claim 2 wherein said second support strut is pivotally attached to said neck collar.

4. The orthosis of claim 2 wherein said neck collar further comprises
   a second supporting member; and
   an occipital support coupled to said second supporting member.

5. The orthosis of claim 2 further comprising attachment straps coupling said pressure bearing chest pad and said pressure bearing back pad.

6. The orthosis of claim 5 wherein said attachment straps form a detachable coupling mechanism.

7. The orthosis of claim 1 wherein said support strut comprises a single rod having two end portions coupled to said neck collar.

8. The orthosis of claim 7 wherein said two end portions of said single rod are coupled to said neck collar at said first supporting member.

9. An apparatus for limiting a patient's neck motion comprising:

an adjustable collar including a chin support mechanism and a load bearing member coupled to said chin support;

a load bearing chest plate;

a support strut mechanism comprising a single rod bent to form a u-shape at a portion of the rod adjacent to the load bearing chest plate;

a first coupler attaching a first end of said support strut mechanism to said adjustable collar at said load bearing member; and a second coupler attaching a second end of said support strut mechanism to said load bearing chest plate; and wherein said first coupler and said second coupler permit said second end of said support strut mechanism to move relative to said adjustable collar and said load bearing member of said adjustable collar is adapted to contact an upper chest area of a patient when worn.

10. The apparatus of claim 9 wherein said support strut mechanism has two end portions coupled to said adjustable collar at said load bearing member.

11. The apparatus of claim 10 wherein said two end portions of said support strut mechanism are coupled to an area of said load bearing member adapted to contact the upper chest area of the patient.

* * * * *